United States Patent [19]

Adolf

[11] Patent Number: 4,791,101
[45] Date of Patent: Dec. 13, 1988

[54] SYNERGISTIC MIXTURES OF INTERFERONS AND TUMOR NECROSIS FACTOR

[75] Inventor: Gunther Adolf, Vienna, Austria

[73] Assignee: Boehringer Ingelheim, Fed. Rep. of Germany

[21] Appl. No.: 746,793

[22] Filed: Jun. 20, 1985

[30] Foreign Application Priority Data

Jun. 23, 1984 [DE] Fed. Rep. of Germany ....... 3423234

[51] Int. Cl.⁴ .............................................. A61K 37/02
[52] U.S. Cl. .......................................... 514/2; 514/12; 424/95
[58] Field of Search ......................... 424/95; 514/2, 12

[56] References Cited

FOREIGN PATENT DOCUMENTS 84303652.6 12/1984 European Pat. Off. .
84107242.4 1/1985 European Pat. Off. .
3227262.6 3/1983 Fed. Rep. of Germany .

OTHER PUBLICATIONS

Kita et al–Chem. Abst., vol. 93 (1980), p. 93379p.
Mitsuhashi et al–Chem. Abst., vol. 98 (1983), p. 204393p.
Umeda et al–Chem. Abst., vol. 99 (1983), p. 153,665q.
Williams et al., *The Journal of Immunology:* 130, No. 2 (1983), pp. 518–520.
Lee et al., *The Journal of Immunology:* 138, No. 3 (1983), pp. 1083–1086.
Rubin et al., *Proc. Natl. Acad. Sci.*, USA, 82:6637–6641 (Oct. 1985).
Williamson et al, "Human Tumor Necrosis Factor Produced by Human B-Cell Lines: Synergistic Cytotoxic Interaction with Human Interferon," *Proc. Natl. Acad. Sci.*, USA, 80: 5397–5401 (1983).
Czarniecki et al, "Synergistic Antiviral and Antiproliferative Activities of Escherichia Coli-Derived Human Alpha, Beta, and Gamma Interferons," *J. Virol.*, 49(2): 490–496 (1984).
Scorticatti et al, "Systemic Ifn-Alpha Treatment of Multiple Bladder Papilloma Grade I or II Patients: Pilot Study," *J. Interferon Res.*, 2(3): 339–343 (1982).
Taylor–Papdimitriou et al, "Effects of HuIFN-x2 and HuIFN-x (Namalwa) on Breast Cancer Cells Grown in Culture and as Xenografts in the Nude Mouse," *J. Interferon Res.*, 2(4): 479–491 (1982).
Quesada et al, "Clinical and Immunological Study of Beta Interferon by Intramuscular Route in Patients with Metastatic Breast Cancer," *J. Interferon Res.*, 2(4): 593–599 (1982).
Paraf et al, "Differential Cytostatic Effect of Interferon on Murine BALB/c B- and T-Cell Tumors," *J. Interferon Res.*, 3(2): 253–260 (1983).
Balkwill et al, "An Animal Model System for Investigating the Anti Tumor Effects of Human Interferon," *J. Interferon Res.*, 3(3): 319–326 (1983).
Matheson et al, "Effect of Fibroblast-Derived Interferon Administration on Immune Responsiveness in a Patient with Nasopharyngeal Carcinoma," *J. Interferon Res.*, 3(4): 437–441 (1983).
Gresser et al, "Inhibitory Effect of Mouse Interferon on the Growth of an Embryonal Carcinoma in Mice," *J. Interferon Res.*, 4(3):375–381 (1984).
Hokland et al, "Effect of Recombinant Alpha Interferon on NK and ADCC Function in Lung Cancer Patients: Results from a Phase II Trial," *J. Interferon Res.*, 4:561–569 (1984).
Carswell et al, "An Endotoxin-Induced Serum Factor That Causes Necrosis of Tumors," *Proc. Nat. Acad. Sci.*, USA, 72(g): 3666–3670 (1975).

(List continued on next page.)

*Primary Examiner*—Sam Rosen
*Attorney, Agent, or Firm*—Saidman, Sterne, Kessler & Goldstein

[57] ABSTRACT

Ternary compositions of an interferon of the alpha and/or beta type with an interferon of the gamma type and tumor necrosis factor having a surprising and unexpected synergistic anti-proliferative effect on neoplastic cells when compared to the activity of the individual components of this invention, said compositions being useful in the treatment of neoplasia in animals including humans.

27 Claims, 4 Drawing Sheets

OTHER PUBLICATIONS

Helson et al, "Effects of Murine Tumor Necrosis Factor on Heterotransplanted Human Tumors," *Expl. Cell Biol.*, 47: (1979).

Kull and Cuatrecasas, "Preliminary Characterization of the Tumor Cell Cytotoxin in Tumor Necrosis Serum", *J. Immunol.*, 126(4):1279–1283 (1981).

Haranaka et al, "Antitumor Activity of Murine Tumor Necrosis Factor (TNF) Against Transplanted Murine Tumors and Heterotransplanted Human Tumors in Nude Mice," *Int. J. Cancer*, 34:263–267 (1984).

Hakla and Rustum, "The Potential Value of *In Vitro* Screening," *Meth. Cancer Res.*, XVI:247–287 (1979).

National Cancer Institute Monograph No. 55 (NIH Publication No. 80-1933), "Experimental Evaluation of Anti-Tumor Drugs in the USA and USSR and Clinical Correlations" (1980).

Cowan and Von Hoff, "The Human Tumor Cloning Assay: An In Vitro Assay for Anti-Tumor Activity in Solid Tumors," in, *Cancer Chemotherapy I*, F. M. Muggia, ed., pp. 103–121, Table 3 at p. 113 (1983).

Tanneberger et al, "Pretherapeutic In Vitro Prediction of Human Tumor Drug Response," in *Cancer Chemotherapy and Selective Drug Development*, K. R. Harrap et al., p. 517 (1984).

Salmon, "Pre-Clinical and Clinical Applications of Chemosensitivity Testing with a Human Tumor Colony Assay," in *Human Tumor Cloning*, S. Salmon and J. Trent, Eds., pp. 499–508 (1984).

Venditti, "The National Cancer Institute Antitumor Drug Discovery Program, Current and Future Perspectives: A Commentary," *Cancer Treatment Reps.*, 67(9): 767–772, at 768 (1983).

Gray et al, *Nature*, 312: 721–724 (1984), "Cloning and Expression of cDNA for Human Lymphotoxin, A Lymphokine with Tumor Necrosis Activity".

Pennica et al, *Nature*, 312:724–729 (1984), "Human Tumor Necrosis Factor: Precursor Structure, Expression and Homology to Lymphotoxin".

Imanishi et al, "Production and Characterization of Human Tumor-Degenerating Factor (TDF)", *Chem. Abstr.*, 100: 49841x (1984).

SYNERGISTIC MIXTURES OF INTERFERONS AND TUMOR NECROSIS FACTOR

BACKGROUND OF THE INVENTION

1. Field of the Invention

This invention is directed to the discovery that binary compositions of an interferon of the alpha, beta or gamma type with tumor necrosis factor, and ternary compositions of an interferon of the alpha and/or beta type with an interferon of the gamma type and tumor necrosis factor have a surprising and unexpected synergistic anti-proliferation effect on neoplastic cells when compared to the activity of the individual components of this invention. The compositions of the present invention are of use in the treatment of neoplasia in animals including humans.

2. Description of the Background Art

A number of proteins occurring naturally in higher organisms are capable of inhibiting the proliferation of tumor cells in vitro and in vivo. These include, inter alia, interferons, lymphotoxins and tumor necrosis factors.

Interferons are divided into three classes differing in their biological and physico-chemical properties. Alpha-interferons (IFN-alpha) include, in humans and a number of other mammals investigated up to now, a family of proteins which are very similar to one another in amino acid sequence and in properties. See, e.g., Stewart, W. E., *The Interferon System*, Springer Verlag, Wein-New York (1981); Weissmann, C., in *Interferon 1981* (Gresser, I., Ed.), pp. 101–154, Academic Press, London (1981); Weck, P. K. et al., *J. Gen. Virol.*, 57:233–237 (1981). Beta-Interferons (IFN-beta) are represented by a single protein in humans and in the majority of other species of mammals investigated. However, a number of IFN-beta subtypes are present in cattle. Wilson, V. et al., *J. Mol. Biol.*, 166:457–475 (1983). Human IFN-beta shows partial sequence homology with human IFN-alpha. Both are relatively acid-stable, and appear to bind to the same membrane receptor. However, human IFN-beta may be differentiated from IFN-alpha, for example, by serological means and by its spectrum of activity on heterologous cells. Stewart, W. E., *The Interferon System*, Springer Verlag, Wein-New York (1981). Gamma-interferon (IFN-gamma), which is coded for by a single gene in man and in all other species investigated hitherto, is unrelated or only very distantly related to IFN-alpha and IFN-beta in its amino acid sequence. Furthermore, IFN-gamma is acid-unstable and differs clearly from IFN-alpha and IFN-beta in other properties as well. See, Steward, W. E., *The Interferon Systems*, Springer Verlag, Wein-New York (1981); Epstein, L. in *Interferon 1981* (Gresser, I., Ed.), pp. 13–44, Academic Press, London (1981); Gray, P. W. et al., *Nature*, 295:503–508 (1982); Gray, P. W. & Goeddel, D. V., *Proc. Natl. Acad. Sci., USA*, 80:5842–5845 (1983).

As a result of these differences, IFN-alpha and IFN-beta are referred to in the literature as type I interferons, while IFN-gamma is referred to as a type II interferon. All these interferons, however, have antiviral activity and a number of immune-modifying activities. Friedman, R. M. and Vogel, S. N., in *Advances in Immunology*, 34:97–140, Academic Press, London (1983). Type I and type II interferon mixtures show a synergistic activity in various systems. Czarniecky, C. W. et al., *J. Virol.*, 49:490–496 (1984).

Recently, progress in molecular biology has allowed the cloning and production of all classes of human interferons in microorganisms. As a result, it has been possible for the first time to produce sufficiently large quantities of interferons, purified to homogeneity, for the treatment of human diseases in clinical trails. However, the reports of human clinical trails indicate that, in a number of malignant diseases, therapy is unsuccessful or has produced only unsatisfactory results. Moreover, it has been observed that it is often impossible to improve the therapeutic results by increasing the dosage of IFN administered owing to the intolerable side effects which result. Sikora, K. and Smedley, H., *Br. Med. J.*, 286:739–740 (1983); Jones, D. H. et al., *Br. J. Cancer*, 47:361–366 (1983); Marna, G. et al., *J. Biol. Resp. Modif.*, 2:343–347 (1983).

Tumor necrosis factor (TNF) was originally described as a protein which can be induced in Bacillus Calmette-Guerin-sensitized animals by endotoxin treatment. Carswell, E. A. et al., *Proc. Natl. Acad. Sci., USA*. 72:3666–3670 (1975). TNF shows cytostatic and/or cytotoxic effects on a number of tumor cell lines in vitro and, in animal models, brings about hemorrhagic necrosis of certain transplantable tumors.

Human B-lymphoblastoid cells lines are known to release a number of lymphokines, including IFN-alpha, macrophage activating factor, migration inhibitory factor and skin reactive factor (Schook, L. B. et al., in *Lymphokines: A Forum for Immunoregulatory Cell Products* (Pick, E. & Landy, M., Eds.), Vol. 2, pp. 1–19, Academic Press, New York (1981); McEntire, J. E. et al., in *Lymphokines and Thymic Hormones: Their Potential Utilization in Cancer Therapeutics* (Goldstein, A. L. & Chirigos, M. A., Eds.), pp. 109–119, Raven Press, New York (1981)). Recently, it has been reported that these cells lines also spontaneously produce a protein which, according to various criteria, may be designated human tumor necrosis factor (Hu-TNF). Williamson, B. et al., *Proc. Natl. Acad. Sci., USA*, 80:5397–5401 (1983). Partially purified culture supernatants of human B-lymphoblastoid cells have shown a synergistic anti-proliferative activity with human IFN-alpha or IFN-gamma. Williamson, B. et al., supra. However, partially purified culture supernatants such as used by Williamson et al. contain many different lymphokines, as noted above, as well as many other potentially unknown impurities. As a result, the true identity of the agent or factor present in these supernatants responsible for the synergistic anti-proliferative activity observed has hitherto been unknown. Thus, the unavailability of a highly purified form of the active agent present in human B-lymphoblastoid cell supernatants has deprived the medical arts of a potentially powerful tool for the treatment of neoplastic disease in man and animals. A need, therefore, has continued to exist to identify the active agent which could then be used in highly purified form along with highly purified human type I and/or type II interferons for disease treatment in man and animals.

SUMMARY OF THE INVENTION

Recognizing that Hu-TNF was possibly the active agent present in partially purified B-lymphoblastoid cell supernatants responsible for the synergistic anti-proliferative activity observed when said supernatants were applied in admixtures with human interferon-alpha or interferon-gamma, the inventors sought to investigate the effect of the use of highly purified Hu-TNF in admixture with interferons, and to prepare admixtures of these compounds for the treatment of neoplastic disease in man. As a result of their efforts, it has been discovered that certain binary compositions of an interferon of the alpha, beta or gamma type with tumor necrosis factor and certain ternary compositions of an interferon of the alpha or beta type with an interferon of the gamma type and tumor necrosis factor, all of the above individually in highly purified form, have a surprising and unexpected synergistic cytostatic and/or cytotoxic effect. The binary and ternary compositions are useful for the treatment of neoplastic disease in man.

DESCRIPTION OF THE DRAWINGS

A more complete appreciation of the invention and many of the attendant advantages thereof will be readily obtained as the same become better understood by reference to the following detailed description when considered in connection with the accompanying drawings, which show the effects of highly purified Hu-TNF, IFN-alpha, IFN-beta, and IFN-gamma, alone and/or in various combinations, on the doubling of cell lines in tissue culture, the experiments being conducted in parallel. The bars in the figures show the higher of the two individual values. Arrows in the diagram indicate fewer than 10,000 cells counted per culture dish. The various dosages of the different components and combinations used are also indicated. Specifically.

In all of the above-described figures, the synergistic effect of the combination of Hu-TNF and interferons will be evident to those of skill in the art.

DESCRIPTION OF THE PREFERRED EMBODIMENTS

By "anti-proliferation" is meant cytostatic and/or cytotoxic action upon cells. "Cytostatic" refers to the characteristic of suppressing the growth or multiplication of cells. "Cytotoxic" refers to the characteristic of having a specific toxic action upon cells of organs.

By "synergism" is meant that the combined action of two or more agents is greater than the sum of the actions of each of the agents used alone.

By "synergistically effective amount" is meant an amount of one component of the present invention sufficient to produce a synergistic anti-proliferative action when used in combination with another component or components of the present invention.

By "animal origin" is meant a compound of the present invention derivable from a natural animal organism, the term being intended to comprehend the highly purified forms of the compounds produced by any means known to the art, and including production by genetic engineering techniques of the compounds, and compounds analogous thereof. More preferably, "animal orgin" refers to animals of the class Mammalia, and even more preferably, to primates, including humans.

By "produced by recombinant DNA methods" is meant the production by expression of a gene in a host carrying a recombinant DNA molecule containing the sequence for the compound or substance desired to be produced, the term encompassing the necessary and ancillary techniques of genetic engineering which are known in the art.

By "neoplasia" is meant the progressive multiplication of cells under conditions that would not elicit, or would cause cessation of, multiplication of normal cells. Thus, "neoplasm" refers to any new and abnormal growth; specifically, to a new growth of tissue in which the growth is uncontrolled and progressive. Malignant neoplasms are distinguished from benign in that the former show a greater degree of anaplasia and have the properties of invasion and metastasis (transfer of disease from one organ or part thereof to another not directly connected therewith). It will be appreciated that the therapeutic use of the present invention comprehends both malignant and benign neoplasia, with the preferred use in instances of malignant neoplasia.

Principles of neoplasia diagnosis and management are well known in the art. See, e.g., *Harrison's Principles of Internal Medicine,* Petersdorf, R. G. et al., eds., 10th Edition, McGraw-Hill, New York, Section 9, Chapters 124 & 125, pp 751–787 (1983).

The compositions of the present invention require the availability of Hu-TNF of significantly greater (>90%) purity than has heretofore been available. Recently, a new process for preparing Hu-TNF from cells of a permanent B-lymphoblastoid line in a purity of more than 90% has been developed. This process is set forth in the German Patent Application AZ No. P3421731.2, the entire disclosure of which is incorporated herein by reference in its entirety as though set forth below.

Briefly, this process involves the cultivation, in a suitable serum-containing medium, of the human B-lymphoblastoid cell line RPMI-1788/EBI, deposited at the CNCM in Paris, France under Serial No. I-305 on May 23, 1984. After initial proliferation, the cell line is transferred into serum-free medium and stimulated with a suitable tumor promoter, such as mezerein. The methods of cultivating cell lines, and the suitable media involved therein, are well known to those of skill in the art.

In order to achieve the high degree of purity (greater than or equal to 90%), the Hu-TNF is purified by means of pore-controlled glass (CPG) and by anion exchange and lectin affinity chromatography. By this purification process, about 0.1–0.2 mg of Hu-TNF can be obtained from one liter of cell culture, so that for the first time, it has become possible to characterize precisely the biological properties of Hu-TNF and to investigate its effects in admixtures with interferons.

Recently, cDNAs for two human cytotoxic proteins have been cloned in *E. coli* (Gray, P. W. et al., *Nature,* 312: 721–724 (1984); Pennica, D. et al., *Nature,* 312: 724–729 (1984). As is obvious from the amino acid sequences deduced from the DNA sequences, one of these proteins is identical to the natural TNF used in the present invention. Both proteins have very similar biological activities, and their amino acid sequences show a high degree of homology. It is to be expected, therefore, that both proteins share the synergistic interactions with interferon as disclosed herein.

The anti-proliferative (cytostatic/cytotoxic) activity of admixtures of Hu-TNF and IFN was determined as follows: transformed cells originating from humans and mice were grown in the presence of type I IFN or type II IFN of the respective species, and in the presence of Hu-TNF and combinations of these substances. After 5–6 days of growth, the numbers of cells in the cultures were determined and compared with the number of cells in untreated control cultures.

It was found that a combination of highly purified (>90%) Hu-TNF with type I IFN or type II IFN has a higher cytostatic and/or cytotoxic effect than could be expected from adding together the effects of the individual components, i.e., an unexpected synergistic anti-proliferative effect was observed when the combination was used.

Also unexpected was the discovery that a mixture of a composition of all three substances has a higher cytostatic and/or cytotoxic activity than could have been predicted on the basis of the activities of the three binary mixtures. These results demonstrate that in vitro anti-proliferative (cytostatic/cytotoxic) effects can be achieved with the described compositions which would otherwise be achievable only by the use of extremely high doses or the individual components, and which would be intolerable due to undesirable side effects such as described above. Moreover, use of the above-described binary and ternary compositions results in anti-proliferative activity which cannot be achieved even with high doses of the individual components of the compositions described.

This surprising and unexpected synergistic activity was achieved by the use of highly purified (greater than or equal to 98%) human interferons. These may be obtained by any means known to the art, including from genetically engineered bacteria (Gray, P. W. et al., *Nature*, 295:503–508 (1982); Dworkin-Rastl, E. et al., *Gene*, 21:237–248 (1983). This surprising and unexpected synergistic activity was also achieved by highly purified (greater than or equal to 95%) mouse interferons. These may be obtained by any means known to the art, including from genetically engineered bacteria (Gray, P. W. and Goeddel, D. V., *Proc. Natl. Acad. Sci., USA*, 80:5842–5846 (1983)). This surprising and unexpected synergistic activity was also achieved by highly purified (greater than or equal to 90%) Hu-TNF. This may be obtained by any means known to the art, including being prepared as described above and in the incorporated German patent application AZ P3421731.2.

Thus, "highly purified" used with reference to interferon signifies purity greater than or equal to 90%; more preferably, greater than or equal to 95%; and even more preferably, greater than or equal to 98%. "Highly purified" used with reference to tumor necrosis factor signifies purity greater than or equal to 90%; more preferably, greater than or equal to 95%; and even more preferably, greater than or equal to 98%.

As a result of the above-described efforts and experiments of the inventors, it will be appreciated that the characteristic activities and unexpected beneficial synergistic result of the use of highly purified Hu-TNF in combinations with interferons, also highly purified, are the characteristic results of those named compounds, and are not caused by any impurities which might have been present in the preparations or in the partially purified B-lymphoblastoid cell culture supernatants. Those of skill in the art will also appreciate that combinations of human interferons and Hu-TNF in highly purified form will be of great use in the therapy and treatment of neoplastic diseases in man and other mammals.

The highly purified active Hu-TNF and highly purified interferons of the present invention exhibit profound effects on the inhibition of growth of cancer cell lines and tumors including, but not limited to, cervical cancer, lung cancer and melanomas. Other cancers that may be treated by the present invention include breast, anal, colorectal, head, neck and cancers of other body organs. The active Hu-TNF and interferon compositions of the present invention can be administered to animal cells, including human cells, in vivo or in vitro.

Thus, administration to a patient suffering from a neoplastic disease can be intraperitoneal (if disease is at a stage where ascites fluid is present), intratumoral or by injection (if a mass is present), or by profusion into a tumor-adjacent artery. Dosages will depend on the age of the patient, side effects, condition of the patient, advanced stage of the carcinoma, and other such factors readily determined by those skilled in the art. Obviously, the higher the purification of the components administered, the less dosage will be needed to achieve an equivalent result. Also within the contemplation of the present invention is the administration of the respective compounds as a continuous infusion, in order to maintain relatively constant blood and/or tissue concentrations at such a level as one of skill in the art will consider desirable given the condition of the patient and other such factors as described above.

The term "administer" includes any and all means by which an effective amount of the active agents can be introduced into the system of the animal to be treated. Such methods include but are not limited to oral administration, as well as administration parenterally, the active agent or agents dissolved in or compounded with a suitable pharmaceutical carrier. The compounds can be employed in dosage forms such as tablets, capsules, powder packets, or liquid solutions, suspensions or elixirs if used for oral administration. Sterile liquid formulations such as suspensions or solutions can be prepared for parenteral use. In such compositions the active agent or agent will normally be present in an amount of at least 0.5% by weight, based on the weight of the composition, and up to 99.5% by weight thereof. Intramuscular intravenous and intraperitoneal injections are the preferred methods of introducing the active agents of the present invention.

The compounds of the present invention may be administered together or separately in a manner allowing control of the dosage at the target cells, and to optimize the therapeutic effect thereof. For example, if the components of the present invention are administered separately, the administration may be simultaneous, alternate, in parallel, continuous, or a combination of the above, as the practitioner of skill considers indicated in the particular case. Of course, if the components of the present invention are administered together, their relative proportions may be adjusted according to the needs of the patient to whom administered.

The compounds of the present invention may be administered by any means effecting palliating conditions in animals. For example, administration may be parenteral, i.e., subcutaneous, intravenous, intramuscular, or interperitoneal. Parenteral compositions suitable for the practice of the present invention include the active agents in combination with a pharmaceutically acceptable carrier, solvent, or diluent. Typical vehicles for parenteral administration of the active ingredients include aqueous vehicles, water-miscible vehicles such as ethyl alcohol, polyethylene glycol and polypropylene glycol, and nonaqueous vehicles such as corn oil, cotton seed oil, peanut oil, sesame oil, ethyl oleate, isopropyl myristate and benzyl benzoate. Typical parenteral preparations are described in *Remington's Pharmaceutical Sciences*, Mack Publishing Company, Easton, Pennsylvania, 16th Edition, Chapter 84 (1980).

Therapeutic methods of use of the present invention comprehend administering to target cells synergistically effective amounts of tumor necrosis factor and type I and/or type II interferons by methods including but not limited to those described herein, said target cells being located in vivo, in situ, and/or in vitro. Synergistically effective amounts of tumor necrosis factor will range from 0.1–1000 ug/kg body weight, more preferably from 1–100 µg/kg body weight. Synergistically effective amounts of type I and/or type II interferon will range from $10^3$–$10^6$ IU/kg body weight, more preferably from $10^4$–$10^5$ IU/kg body weight. It will be appreciated that the actual dosages used in the treatment of neoplasias will vary as a function of the purity of the preparations, the mode of administration, the condition of the patient and other factors including but not limited to those described herein, these being obvious to those of skill.

Having now generally described this invention, the same will be better understood by reference to certain specific examples which are included herein for purposes of illustration only and are not intended to be limiting of the invention unless otherwise specified. Particularly, it is noted that, in principle, the present invention applies to all interferons and all TNFs, from human and other animal sources, provided that they satisfy the purity criteria, and also to preparations of the above-identified compounds obtained by methods other than those disclosed herein.

EXAMPLE 1

Inhibiting the Proliferation of the Human Cervical Cancer Cell Line Hela

Cells of the human cervical cancer line Hela (Gray, G. D. et al., Cancer Res., 12:264 (1952)) were grown in Eagne's Minimum Essential Medium (Eagle, H., Science, 130: 432 (1959)) in the presence of 10% of fetal calves' serum, penicillin (100 units/ml) and streptomycin (50 units/ml) at 37° C. in a water vapor-saturated atmosphere of 5% $CO_2$ in air. 50,000 cells in 2.5 ml of medium were placed in each 3 cm plastic tissue culture dish; two dishes received added interferons, TNF or combinations of these substances in 0.5 ml of medium. Two dishes received only the medium; these cultures were used as a control for the growth of untreated cells. The dishes were incubated for six days as described above, then the cells were released from the substrate using trypsin and the number of viable cells was determined using haemocytometer chambers.

The following interferon and TNF preparations were used:
(a) Human IFN-alpha-2-arg ("IFN-alpha"), produced in *E. coli* (Dworkin-Rastl, E. et al., Gene, 21: 237–248 (1983)), purity at least 98%, specific activity $300 \times 10^6$ IU/mg (based on the reference standard CO-23-901-527 of the National Institute of Health, USA), manufactured by Boehringer Ingelheim, Ingelheim, FRG. This protein is identical to the interferon described by Streuli et al., Science, 209:1343–1347 (1980), with the exception of the amino acid at position 34 (arginine instead of histidine).
(b) Human IFN-gamma, produced in *E. coli* (Gray, P. W. et al., Nature, 295:503–508 (1982)), purity at least 98%, specific activity $68 \times 10^6$ IU/mg tested with A549 cells and mouse encephalomyocarditis virus, produced by Genentech, Inc., San Francisco, Calif.
(c) Human TNF, purity at least 90%, prepared as described in German Patent Application AZ No. P3412731.2.

Figure 1:
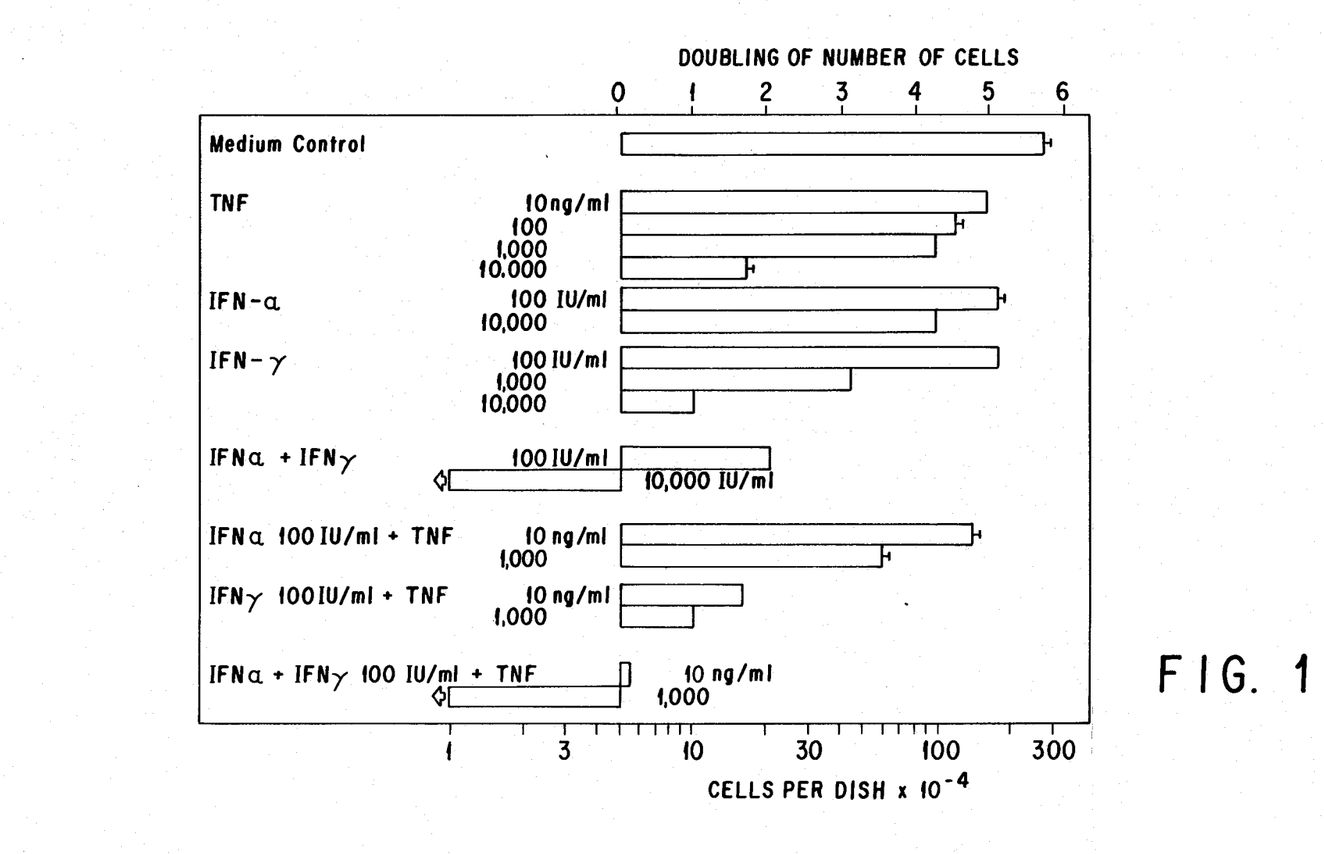
FIG. 1 shows the inhibition of proliferation of human cervical cancer cell line HeLa grown in the presence of Hu-TNF, IFN-alpha, IFN-gamma, IFN-alpha+IFN-gamma, IFN-alpha+Hu-TNF, IFN-gamma+Hu-TNF, IFN-alpha+IFN-gamma+Hu-TNF, or control, the experiment being conducted in parallel.

FIG. 1 shows the results of the test. It shows the geometric average values of the numbers of cells in both cultures which are conducted in parallel. The bars show the higher of the two individual values. Arrows in the diagram indicate that fewer than 10,000 cells were counted per culture dish.

A combination of IFN-gamma (100 IU/ml) with TNF (10 or 1,000 ng/ml) surprisingly showed a significantly higher activity than could be expected on the basis of the activity of the components. More surprisingly, a mixture of IFN-alpha, IFN-gamma (100 IU/ml in each case) and TNF (10 to 1,000 ng/ml) showed a significantly higher activity than could be expected on the basis of the activity of the three binary mixtures.

EXAMPLE 2

Inhibiting the Proliferation of the Human Lung Cancer Cell Line A549

Figure 2:
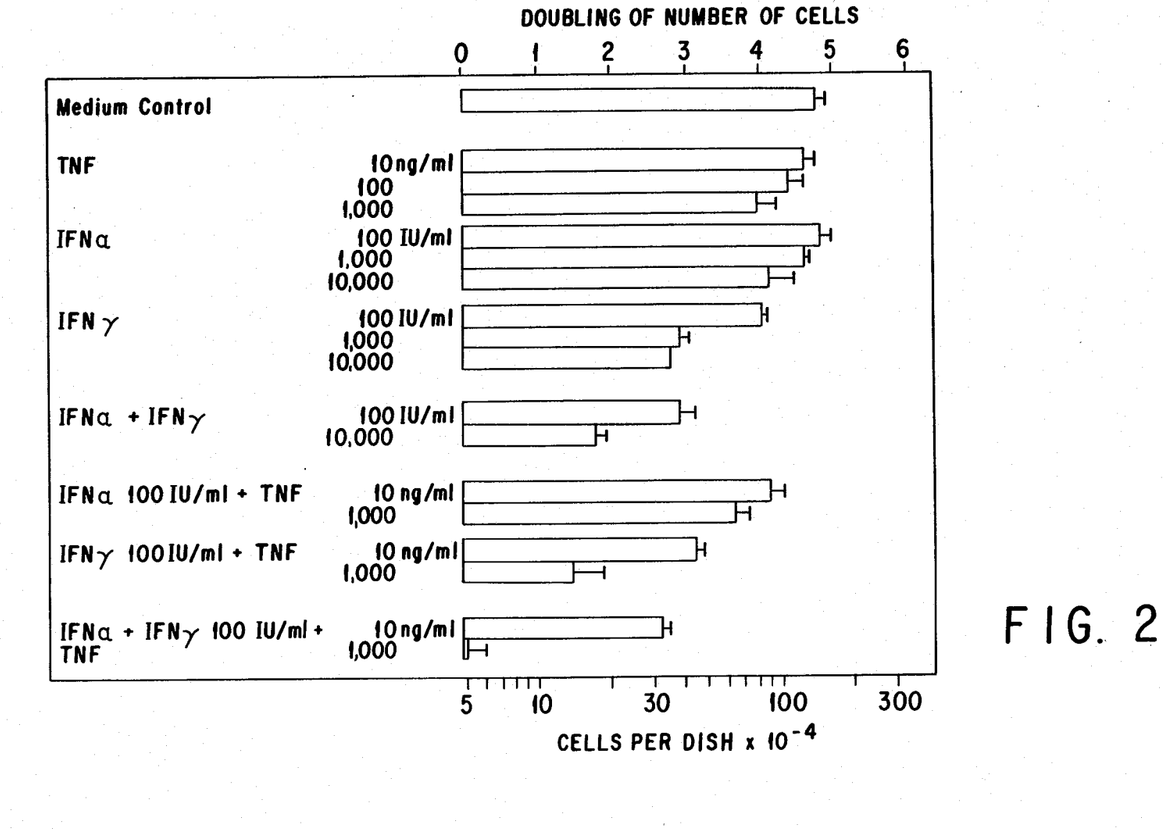
FIG. 2 shows the inhibition of the proliferation of human lung cancer cell line A549 when cultured in the presence of the same components and combinations thereof as described for FIG. 1.

Culture of cells of human lung cancer cell line A549 (Giard, D. J., J. Natl. Cancer Inst., 551:1417–1423 (1973)), and treatment with interferons and TNF were carried out as described in Example 1. The results are shown in FIG. 2.

A combination of IFN-gamma (100 IU/ml) with TNF (10 or 1,000 ng/ml) surprisingly showed a significantly higher activity than could be expected on the basis of the activity of the individual components. More surprisingly, a combination of IFN-alpha with IFN-gamma (100 IU/ml in each case) and TNF (1,000 ng/lm) showed a higher activity than could be expected on the basis of the activity of the three binary mixtures.

EXAMPLE 3

Inhibiting the Proliferation of the Mouse Cell Line L929

Culture of the cells of mouse cell line L929 (Sanford, K. K. et al., J. Natl. Cancer Inst., 9: 229 (1948)) was carried out as described in Example 1. In order to test the inhibition of growth by interferons and TNF, the following preparations were used:
(a) Mouse interferon-alpha/beta, specific activity $44 \times 10^6$ IU/mg, produced by Enzo Biochem, Inc., New York, New York.
(b) Mouse interferon-gamma, produced in *E. coli* (Gray, P. W. and Goeddel, D. V., Proc. Natl. Acad. Sci., USA, 80: 5842–5846 (1983)), purity at least 95%, specific activity $7 \times 10^6$ IU/mg (tested on L929 cells with encephalomyocarditis virus), produced by Genentech, Inc., San Francisco, Calif.

(c) Human TNF, purity at least 90%, prepared as described in the incorporated German Patent Application AZ No. P3421731.2.

Figure 3:
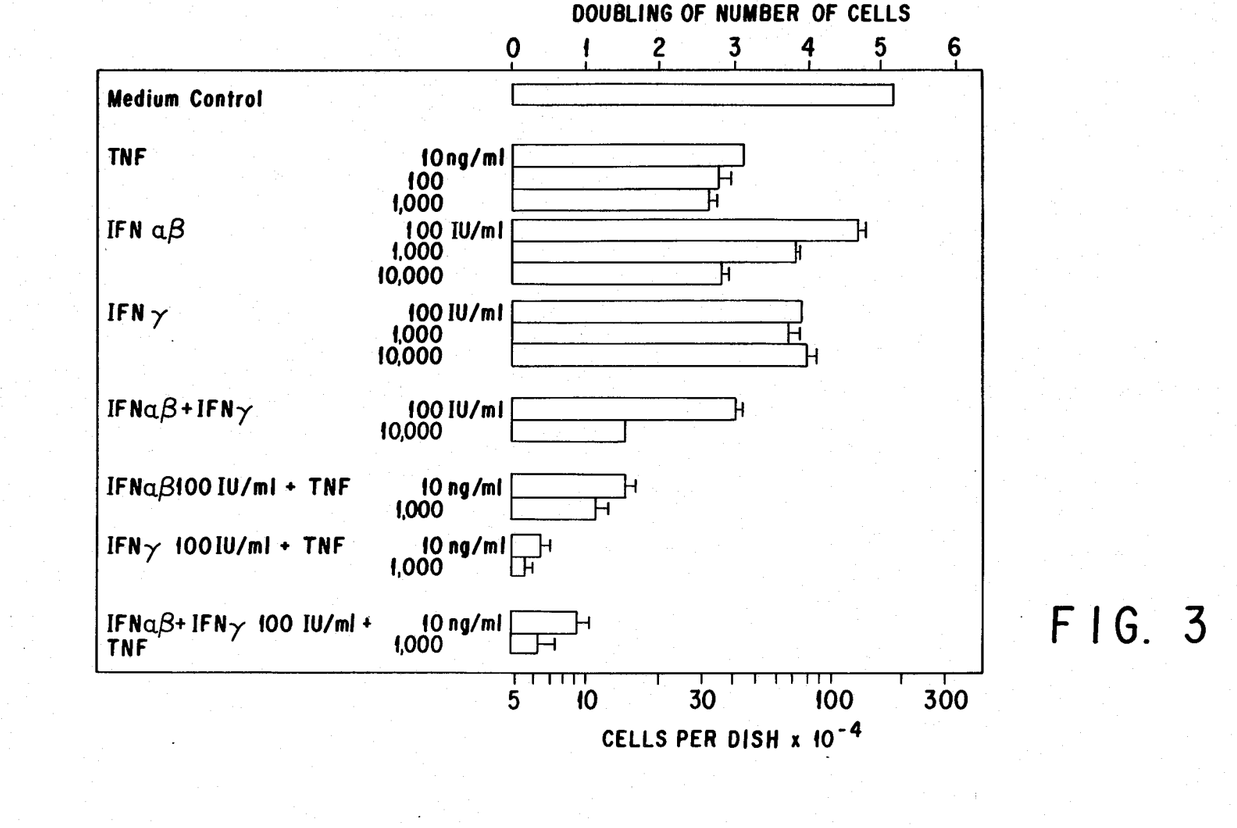
FIG. 3 shows the inhibition of the proliferation of mouse cell line L929 when cultured in the presence of Hu-TNF, IFN-alpha,beta, IFN-gamma, IFN-alpha,-beta+IFN-gamma, IFN-alpha,beta+Hu-TNF, IFN-gamma+Hu-TNF, IFN-alpha,beta+IFN-gamma+-Hu-TNF, or control.

The cells were treated as described in Example 1 and the number of cells was determined after five days. FIG. 3 shows the results obtained.

Treatment of the cells with a mixture of IFN-alpha/-beta (100 IU/ml) and TNF (10 or 1,000 ng/ml) or IFN-gamma (100 IU/ml) and TNF (10 or 1,000 ng/ml) showed a surprisingly greater inhibition of growth than could be expected on the basis of the activity of the components.

EXAMPLE 4

Inhibiting the Proliferation of Melanoma Cell Line B16

Figure 4:
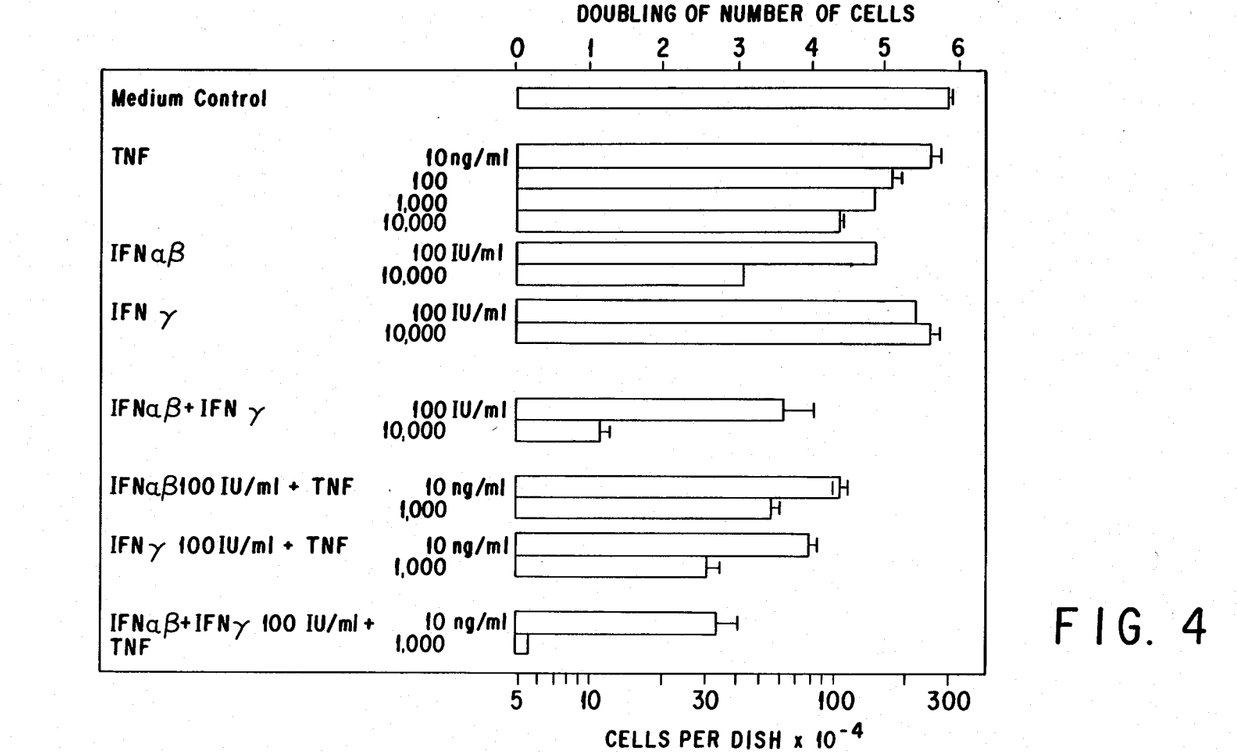
FIG. 4 shows the inhibition of the proliferation of melanoma cell line B16, when cultured in the presence of the same components and combinations thereof as described for FIG. 3.

Culture of mouse melanoma cells (Fidler, I. J., *J. Natl. Cancer. Inst.*, 45:773 (1970)), and treatment with mouse interferons and TNF were carried out as described in Examples 1 and 3. The results are shown in FIG. 4.

Treatment with a combination of IFN-alpha/beta (100 IU/ml) and TNF (1,000 ng/ml) or a combination of IFN-gamma (100 IU/ml) and TNF (10 or 1,000 ng/ml) showed a surprisingly greater activity than could be expected on the basis of the activity of the individual components. A combination of IFN-alpha/-beta (100 IU/ml) showed a higher activity than could be expected on the basis of the activity of the three binary combinations.

Having now fully described the invention, it will be apparent to one of ordinary skill in the art that many changes and modifications can be made thereto without departing from the spirit or scope of the invention as set forth herein.

What is claimed as new and intended to be secured by Letters Patent is:

1. A composition having a synergistic anti-proliferative effect on neoplastic animal cells, comprising a synergistically effective amount of
   (a) highly purified tumor necrosis factor;
   (b) highly purified type I interferon; and
   (c) highly purified type II interferon.

2. A composition having a synergistic anti-proliferative effect on neoplastic animal cells selected from the group consisting of anal, breast, cervical, colorectal, head, lung, melanoma, and neck cancer cells, comprising a synergistically effective amount of
   (a) highly purified tumor necrosis factor;
   (b) highly purified type I inerferon; and
   (c) highly purified type II interferon.

3. The composition of claim 1 or 2, wherein said tumor necrosis factor, said type I interferon and said type II interferon each is greater than or equal to 90% pure.

4. The composition of claim 3, wherein said tumor necrosis factor is of mammalian origin.

5. The composition of claim 4, wherein said tumor necrosis factor is human tumor necrosis factor.

6. The composition of claim 3, said tumor necrosis factor being greater than or equal to 95% pure.

7. The composition of claim 6, said tumor necrosis factor being greater than or equal to 98% pure.

8. The composition of claim 3, wherein said type I interferon is alpha or beta or subtypes thereof, or a mixture thereof.

9. The composition of claim 8, wherein said type I interferon is of mammalian origin.

10. The composition of claim 9, wherein said type I interferon is human type I interferon.

11. The composition of claim 10, wherein said type I interferon is human interferon-alpha-2-arg.

12. The composition of claim 7, said type I interferon being greater than or equal to 95% pure.

13. The composition of claim 12, said type I interferon being greater than or equal to 98% pure.

14. The composition of claim 3, wherein said type II interferon is gamma or a subtype thereof.

15. The composition of claim 14, wherein said type II interferon is of mammalian origin.

16. The composition of claim 15, wherein said type II interferon is human interferon gamma.

17. The composition of claim 14, said type II interferon being greater than or equal to 95% pure.

18. The composition of claim 17, said type II inteferon being greater than 98% pure.

19. The composition of claim 3, further comprising a pharmaceutically acceptable carrier or carriers.

20. The composition of claim 3, wherein said type I interferon is produced by recombinant DNA methods.

21. The composition of claim 3, wherein said type II interferon is produced by recombinant DNA methods.

22. The composition of claim 3, wherein said tumor necrosis factor is produced by recombinant DNA methods.

23. A method for the treatment of neoplastic disease in animals, comprising administering to an animal suffering from or suspected or suffering from said disease a synergistically effective amount of
   (a) highly purified tumor necrosis factor;
   (b) highly purified type I interferon; and
   (c) highly purified type II interferon.

24. A method for the treatment of neoplastic disease selected from the group consisting of anal, breast, cervical, colorectal, head, lung, melanoma, and neck cancer, comprising administering to an animal suffering from or suspected of suffering from said disease a synergistically effective amount of
   (a) highly purified tumor necrosis factor;
   (b) highly purified type I interferon; and
   (c) highly purified type II interferon.

25. The method of claim 23 or 24, wherein said animal is a mammal.

26. The method of claim 25, wherein said mammal is human.

27. The method of claim 23 or 24, wherein the dose of tumor necrosis factor is between 0.1–1000 mg/kg body weight, and wherein the dose of type I and/or type II interferon is between $10^3$ and $10^6$ IU/kg body weight.

* * * * *